United States Patent
Streit et al.

(10) Patent No.: US 8,800,365 B2
(45) Date of Patent: Aug. 12, 2014

(54) METHOD FOR REGISTERING THE FILLING POTENTIAL OF A WASTE CONTAINER OF MICROPLATE WASHING DEVICES

(75) Inventors: Wolfgang Streit, Hallein (AT); Juha Koota, Berchtesgaden (DE); Wolfgang Fuchs, Salzburg (AT)

(73) Assignee: Tecan Trading AG, Mannedorf (CH)

( * ) Notice: Subject to any disclaimer, the term of this patent is extended or adjusted under 35 U.S.C. 154(b) by 337 days.

(21) Appl. No.: 13/357,773

(22) Filed: Jan. 25, 2012

(65) Prior Publication Data

US 2012/0198928 A1 Aug. 9, 2012

Related U.S. Application Data

(60) Provisional application No. 61/437,331, filed on Jan. 28, 2011.

(30) Foreign Application Priority Data

Jan. 28, 2011 (CH) ........................... 150/11

(51) Int. Cl.
*G01F 23/14* (2006.01)
*G01N 35/10* (2006.01)
*G01F 17/00* (2006.01)
*B01L 99/00* (2010.01)

(52) U.S. Cl.
CPC ..... *G01N 35/1004* (2013.01); *B01L 2300/0829* (2013.01); *G01F 23/14* (2013.01); *G01F 17/00* (2013.01); *B01L 99/00* (2013.01)
USPC ......... 73/303; 73/299; 73/863.01; 73/863.31; 73/864.15

(58) Field of Classification Search
USPC .................................................. 73/299, 303
See application file for complete search history.

(56) References Cited

U.S. PATENT DOCUMENTS

| | | | |
|---|---|---|---|
| 4,635,665 | A | 1/1987 | Namba et al. |
| 5,186,760 | A | 2/1993 | Rubenzer |
| 5,535,624 | A | 7/1996 | Lehmann |
| 5,760,294 | A | 6/1998 | Lehmann |
| 5,951,783 | A | 9/1999 | Kontorovich et al. |
| 6,121,049 | A | 9/2000 | Dorenkott et al. |
| 2004/0089330 | A1 | 5/2004 | Muller |
| 2009/0032064 | A1 | 2/2009 | Gifford et al. |
| 2009/0133512 | A1 | 5/2009 | Kuroda |

FOREIGN PATENT DOCUMENTS

| | | |
|---|---|---|
| DE | 4039081 | 6/1992 |
| DE | 19545981 | 6/1997 |
| DE | 19648688 | 5/1998 |
| DE | 19750620 | 6/1999 |
| EP | 2017625 | 1/2009 |
| EP | 1637887 | 7/2009 |
| WO | WO 2005/114116 | 12/2005 |

*Primary Examiner* — Hezron E Wiliams
*Assistant Examiner* — Alexander Mercado
(74) *Attorney, Agent, or Firm* — Notaro, Michalos & Zaccaria P.C.

(57) ABSTRACT

Method for registering filling potential of a waste container of a microplate washing device has a needle for aspirating liquids, a waste container, a pump for generating a partial vacuum and a pressure sensor for determining air pressure in the container, a sensor controller, and a first valve for blocking the line between the needle and the waste container. The pump and needle are connected to the container and the method includes closing the first valve, generating a partial vacuum in a test range, closing a further valve between the container and the pump, opening the first valve, triggering a partial vacuum dissipation in the container, measuring a test time for the partial vacuum dissipation in the test range, comparing the test time to a known threshold time, and deciding that the waste container is fillable or not.

15 Claims, 3 Drawing Sheets

…

Figure 1:
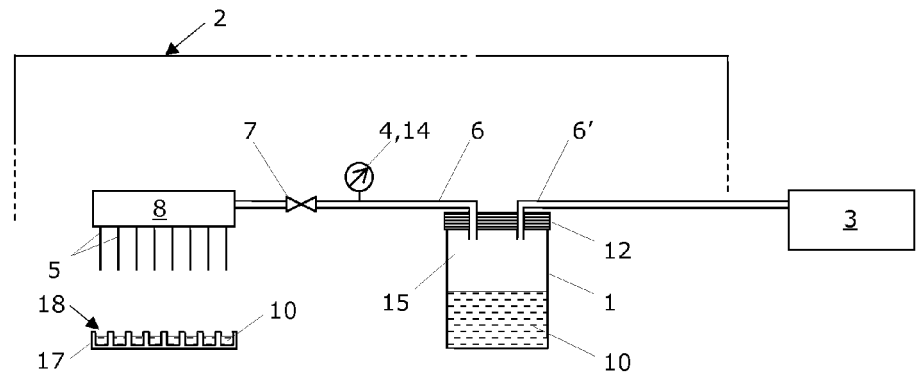

METHOD FOR REGISTERING THE FILLING POTENTIAL OF A WASTE CONTAINER OF MICROPLATE WASHING DEVICES

RELATED PATENT APPLICATIONS

The present application claims priority of the U.S. provisional application No. 61/437,331 and of the Swiss patent application No. 00150/11 both filed on Jan. 28, 2011. The entire disclosure of these two priority defining applications is incorporated herein by explicit reference for any purpose.

RELATED FIELD OF TECHNOLOGY

The invention relates to a method for registering the filling potential of a waste container of a microplate washing device. This washing device comprises at least one washing needle for aspirating liquids and a waste container, which is closable substantially airtight, for catching aspirated liquids. Furthermore, the microplate washing device comprises a pump for generating a partial vacuum resp. under-pressure in the waste container. The pump and the washing needle are each connected via at least one line to the waste container. Finally, the microplate washing device comprises at least one pressure sensor and a sensor controller. The pressure sensor is operationally linked to the waste container for determining an air pressure in this waste container.

RELATED PRIOR ART

Methods for determining air volumes in containers are known per se from the prior art. Such methods are used if, for example, the current fill level in the container or the residual volume, with which the container is still fillable, is to be determined. Based on this determination, it can then, for example, be decided with how much liquid the container can still be filled, or whether the container must be emptied before it is filled further.

Thus, a fill level determination in containers or tank-like vessels is disclosed in the Patent Publication DE 195 45 981 A1. In particular, the degree of filling of liquid containers or silos for storing bulk goods is determined. In the document DE 197 50 620 A1, determining the free volume in an enclosed container (in this case in gasoline tanks of motor vehicles) is disclosed to be carried out in a similar way. Thereby in each case, a container pressure which deviates from the ambient pressure is first set. The time until equalization with the ambient pressure is then determined for the fill level determination. The container fill level is then calculated on the basis of the measured time and the known, theoretical maximum container volume.

A method for registering a fill level quantity of a tank system is known from DE 196 48 688.2. Here, a pressure change is also generated in the tank system using a pressure source. For registering the fill level quantity in this tank system, the time curve of the pressure difference during the pressure buildup or pressure dissipation process is then continuously detected and the fill level is concluded therefrom. Thereby, the tank system comprises a pressure divider arrangement having at least one flow resistance. Thus, if both the level and also tightness are to be checked, additional sensors can be dispensed with.

Alternatively, the fill level can also be determined by means of the hydrostatic pressure, which prevails due to the height of the liquid column in the container. This hydrostatic pressure is then used as a direct measure for the fill level. Similarly thereto, the quantity of the liquid located in a container can be determined by means of weight measurement.

In laboratory technology, the determination of levels in liquid containers is applied in particular in the case of waste containers of laboratory automated equipment, e.g., automated microplate washing devices. Such microplate washers allow washing in an automated way cells, magnetic beads or small biomolecules which are immobilized in the wells of typical microplates using biocompatible liquids such as buffers. The principle of immobilization for cell-based or bead-based assays or for enzyme-linked immunosorbent assays (ELISAs) is well known from the prior art and shall therefore not be repeated at this point. It is also known that during the preparation or performance of such assays, one or more washing steps are typically performed, in which the liquid in individual wells is aspirated and replaced by a fresh liquid by adding (dispensing). During the dispensing, liquid is pressed by means of a pressure pump from one or more storage containers into corresponding lines and discharged via a dispenser needle into a well. In contrast, during the aspiration, the liquid is suctioned out of the well using a suction pump and transferred via separate lines into prepared waste containers.

Since frequently infectious or potentially infectious liquids are transferred from sample vessels into the waste containers during the treatment of cells or during the performance of biological or biochemical assays using biomolecules, it is particularly important here to perform a monitoring as continuously as possible of the fill level in these waste containers. Only in this way it is possible to avoid that an excessively large amount of liquid suctioned from sample vessels is conducted into the corresponding waste containers, these containers then overflowing, and thus a disposal of the infectious or potentially infectious liquids in accordance with the safety requirements is hampered or even made impossible. Typical liquids which are moved by microplate washing devices for washing biological samples are, for example, media for cell cultures, washing buffers, reaction solutions, solvents for biological samples such as nucleic acids, proteins or whole cells, or liquid residues of such biological samples.

So-called floater-based sensors are typically used for the fill level determination in such waste containers of microplate washers. Such a floater is a body having low density and thus floats on the liquid in the container. It is connected to a switch, a sensor, or a displacement pickup (potentiometer), for example. The position of the floater in the liquid container can then be detected by the sensor, for example. Alternatively and in the simplest variant, the floater does not comprise a sensor, but rather is made having a noticeable color, for example, so that the liquid level can be read off directly by eye from the relative height of the float in the container. This allows the operator to monitor directly, how much liquid can still be suctioned out of the sample vessels and transferred into the waste container at the current point in time. Correspondingly, it can then be determined, when the waste container must be replaced to prevent an overflow. The sensor A3413001 from Binsack (Binsack Reedtechnik GmbH, Lämmerspieler Strasse 87-89, 63165 Mühlheim/Main, Germany) is mentioned here as an example of a floater-based sensor known in the prior art, which is commercially available under this name and is used, inter alia, in the microplate washing device with the name Power Washer 384™ of the present applicant for the fill level determination in waste containers.

The use of such floater-based sensors has the advantage that the level of the stored liquid can be read off or measured directly in the container. However, such floater-based sensors, which float on the surface of the waste liquid in the waste container of the microplate washer, are directly exposed to the suctioned-off liquid. Problems can result in particular if, for example, used media of cell cultures or other cell residues are to be transferred into a waste container. Such used media can contain precipitated proteins or suctioned-off cells, which conglomerate and can accumulate as larger, sometimes sticky particles on the sensor arranged in the container. The functionality of the sensor can thus be strongly influenced, or the sensor is even completely blocked. However, if the sensor no longer indicates the correct fill level, the danger in turn exists that too much liquid will be introduced into the waste container, and the liquid will run out of the bottle. This situation is particularly problematic, if biological waste liquids are caught in the waste container, which must be decontaminated, i.e., autoclaved, for example, for correct disposal (e.g., in the case of infectious material/liquid). A system in which such a floater-based sensor is used therefore requires a correspondingly high level of attentiveness and care by the user.

OBJECT AND SUMMARY OF THE PRESENT INVENTION

The object of the present invention is to propose a method, using which it can be registered easily and reliably whether waste liquids can be transferred into waste containers of microplate washers, without the containers overflowing.

This object is achieved according to a first aspect by the features herein disclosed, i.e. by proposing a method for registering the filling potential of a waste container of a microplate washing device. The microplate washing device comprises at least one washing needle for aspirating liquids, a waste container, which is closable substantially airtight, for catching aspirated liquids, and a pump for generating a partial vacuum resp. under-pressure in the waste container. The pump and the washing needle are each connected via at least one line to the waste container. Furthermore, the microplate washing device comprises at least one pressure sensor and a sensor controller, wherein the pressure sensor is operationally linked to the waste container for determining an air pressure therein.

The method according to the invention is characterized in that the microplate washing device further comprises a valve for blocking the line between the washing needle and the waste container, and in that the method comprises the following steps:
a) closing the valve between the washing needle and the waste container and generating a partial vacuum in the waste container at least to a lower limiting pressure of a predetermined partial vacuum test range;
b) blocking the pump-side line to the waste container;
c) opening the valve between the washing needle and the waste container and triggering a partial vacuum dissipation in the waste container;
d) measuring the pressure in the waste container and measuring a test time for the partial vacuum dissipation between the lower limiting pressure up to an upper limiting pressure of the partial vacuum test range, wherein the upper limiting pressure is lower than the ambient pressure;
e) comparing the measured test time to a threshold time determined before the measurement, and
f) deciding that the waste container is not fillable, if the test time falls below the threshold time, or that the waste container is fillable, if the test time is equal to the threshold time or exceeds the threshold time.

Additional preferred and inventive features result from the respective dependent claims.

The present invention comprises the following advantages:
The suction pump function, which is provided as a standard in every microplate washing device, and the internal pressure sensor, which it also comprises, can be used directly for the determination of the current residual volume of the waste container. It can thus be determined reliably and easily "internally in the device", with how much more liquid volume the waste container can be filled, before it must be emptied, without serious technical alterations having to be performed on the device.
Typical disadvantages of floater-based sensor systems for the level determination, such as sticking of the sensors, can be avoided by the simplified construction. This is relevant primarily when working with biological material, such as cells. The method according to the invention therefore provides a significantly more reliable method for determining the current residual volume than the prior art.
In addition to the determination of the air volume in a waste container, the tightness of the washing system can be checked without further structural changes.

BRIEF INTRODUCTION OF THE ATTACHED DRAWINGS

Figure 2:
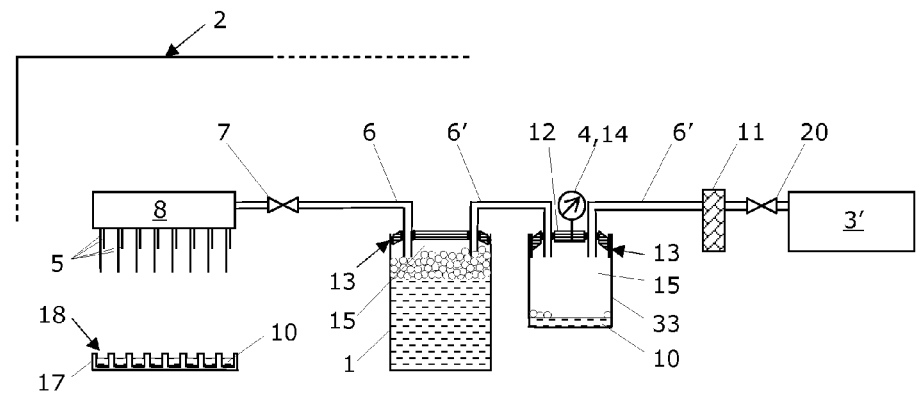
Figure 3:
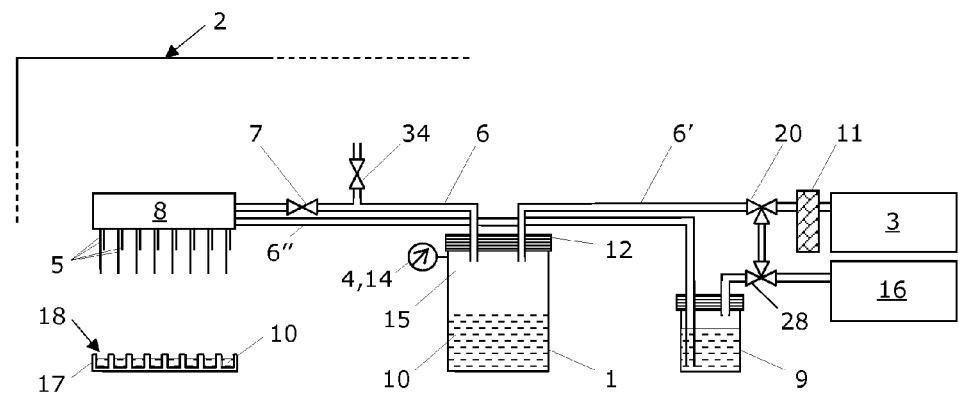
Figure 4:
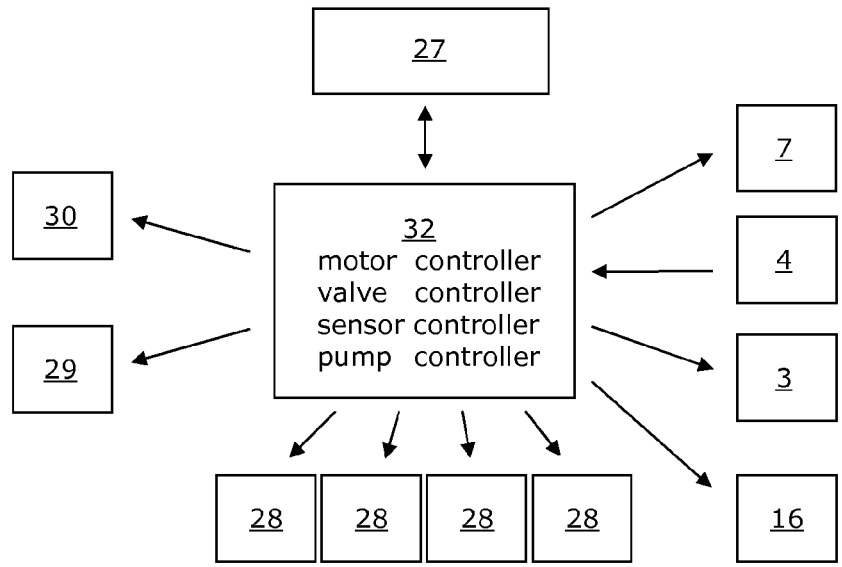
Figure 5:
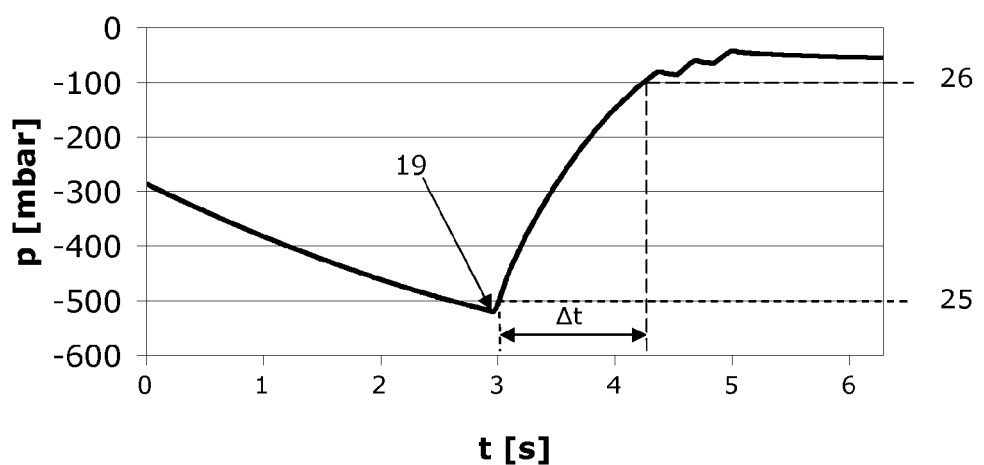
Figure 6:
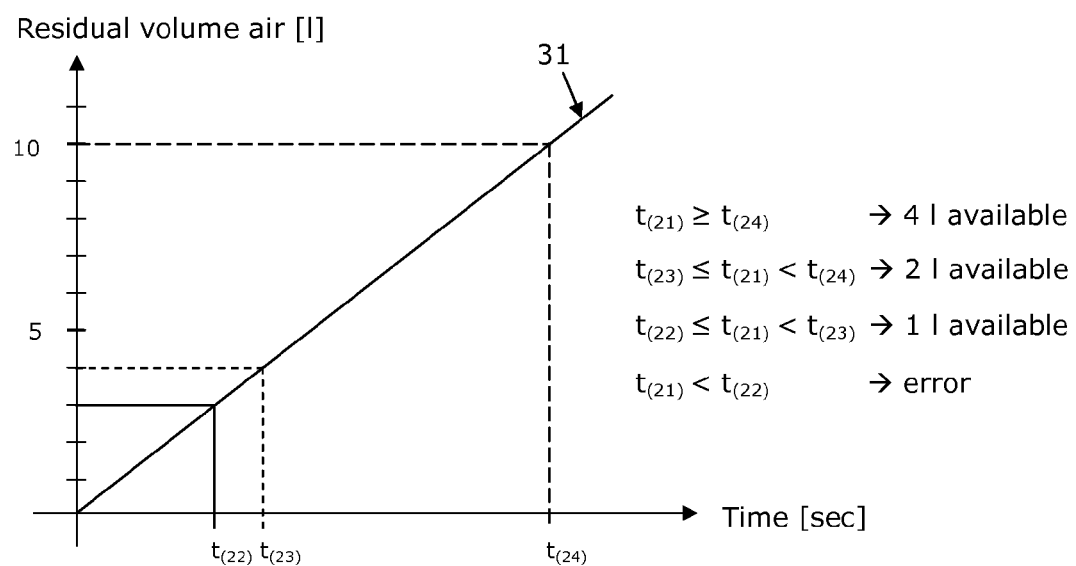

The present invention is explained in greater detail in the following on the basis of the figures appended to this application. These figures disclose preferred variants of a microplate washing device for performing the invention and exemplary measurements using the method according to the invention. The scope of the present invention is not restricted by the figures, however. Combinations of the features of the variants which are shown and/or described are within the scope of the invention. It is shown in:

FIG. 1 an overview illustration of a simple variant of a microplate washing device for performing the method according to the invention and comprising a suction pump and a waste container;

FIG. 2 an overview illustration of a second variant of a microplate washing device for performing the method according to the invention and comprising a combined suction/pressure pump, two waste containers and further optional features;

FIG. 3 an overview illustration of a third variant of a microplate washing device for performing the method according to the invention and comprising a suction pump, a separate pressure pump and further optional features;

FIG. 4 a schematic overview of a circuit diagram of a microplate washing device for performing the method according to the invention;

FIG. 5 an exemplary single measurement of the pressure curve as a function of time for registering the filling potential of a waste container employing partial vacuum;

FIG. 6 a schematic overview of the relationship between residual volume of air in a waste container and corresponding partial vacuum dissipation times in the predetermined partial vacuum test range, having an exemplary determined threshold time, first tolerance time and second tolerance time.

DETAILED DESCRIPTION OF THE PRESENT INVENTION

The fundamental functional principle of microplate washing devices 2 is generally known from the prior art; the Power Washer 384™ platform of the present applicant is mentioned here as an example. Such a microplate washing device 2 comprises one or more storage containers 9 for liquids 10, which are to be dispensed using one or more washing needles 5 into greatly varying sample vessels (wells 18 of a microplate 17). It also comprises one or more waste containers 1, into which liquids 10, which are suctioned out of such sample vessels, are transferred for later disposal. For dispensing liquids 10 in the lines 6" and in the storage container 9 of such a washer 2, a partial vacuum is typically generated by means of a pressure pump 16. In contrast, for aspirating liquids 10, a partial vacuum is generated in the line 6' and in the waste container 1 by means of a suction pump function or a suction pump 3, by which the liquid 10 is suctioned into the washing needle 5, then into the line 6', and finally into the waste container 1.

In connection with the present invention, multiwell plates, which have a plurality of wells or containers which are arranged in an array, are referred to as microplates 17. Especially preferred microplates have, at least approximately, the dimensions and the footprint of a microplate according to the SBS standard, as has been published by the American National Standards Institute (ANSI). For example, microplates, the wells of which are equipped with a round bottom, flat bottom or V-shaped bottom are known. The wells can be implemented as "normal wells", as so-called "deep wells" or also as "low-volume wells". All microplates having the most widely varying well shapes have in common that they have a standardized base area, i.e., a standardized "footprint", and that the axial spacing of the respective wells arranged in an array is also standardized. This axial spacing is, for example, 18 mm in 24 well (4×6) plates, 9 mm in 96 well (8×12) plates, and 4.5 mm in 384 well (16×24) plates. However, plates which only have one large well 18 are also suitable for use in the method according to the invention, as long as they have the typical, standardized microplate footprint.

In the FIGS. 1 to 3, various variants of a microplate washing device 2, which are suitable for performing the method according to the invention, are shown. The individual structural elements of these variants shown can be combined arbitrarily with one another. In addition, the selection and positioning of the individual elements, in particular pressure sensor 4, valve 7, and filter 11, as well as the selection of the line dimensions and their arrangement are within the scope of the knowledge of a person skilled in the art.

FIG. 1 shows an overview of a simplest variant of such a microplate washing device 2. The already provided pump 3 of the microplate washing device 2 is not only used here to aspirate liquids 10 out of sample vessels and to transport these aspirated liquids 10 into the waste container 1, but rather also to register the filling potential of the waste container 1. It is unimportant whether the pump 3 is implemented solely as a suction pump, or whether it is a pump 3 which provides the suction pump function among other functions. Pure suction pumps are, for example, classical vacuum pumps, rotary vane pumps or water jet pumps; thereby vacuum pumps typically have a single valve 20, while rotary vane pumps and water jet pumps typically require a separate valve 20 for the controlling. However, the suction pump function can also be provided by a combined suction/pressure pump 3'. This variant is shown in FIG. 2.

The pump 3 for generating a partial vacuum can be implemented as an internal module of the device, i.e., it can be integrated completely (functionally and structurally) into the microplate washing device 2. Alternatively, the pump 3 of the microplate washing device 2 for generating the partial vacuum can be an external pump, which is functionally connected to the device 2, however, such that the suction pump function forms an inherent part of the microplate washing device 2. As an example, an external house pump is mentioned here, which is connected via corresponding lines 6' ("house vacuum") to the microplate washing device 2 or its waste container 1. In any case, the use of the device-internal suction pump function for the performing of the method according to the invention offers the advantage that large installation and/or reconfiguration measures do not have to be performed on the device and thus the complexity of the microplate washing device 2 can be kept low.

If an overpressure is alternatively applied to perform the method according to the invention instead of the use of partial vacuum, the pressure pump function 16 provided for dispensing in every microplate washing device 2 can be used to register the filling potential of the waste container 1. FIG. 3 shows a microplate washing device 2 in its entirety, having both the aspiration function and the dispenser function. If the pump 3 of the microplate washing device 2 used for the aspiration is implemented as a combined suction/pressure pump 3', as shown in FIG. 2, either a partial vacuum can be generated in the waste container 1 or alternatively an overpressure can be generated therein using the same pump 3'.

Usable pumps or pump systems for generating a partial vacuum are well known from the prior art. For example, the Thomas diaphragm pump of the type 8011 ZVP 35 (Gardner Denver Thomas GmbH, Benzstrasse 28, 82178 Puchheim, Germany) is mentioned here as a pump 3 of the microplate washing device which is well suitable for performing the method according to the invention.

A washing head 8 having a row of eight washing needles 5 is schematically shown in FIG. 1. Liquid can be suctioned simultaneously out of all wells 18 of a row of eight using this washing head 8 and the suction pump function.

Washing heads 8 having a row of eight washing needles 5 for aspirating liquids 10 and additionally eight washing needles 5 for dispensing liquids 10 are also known and shown in FIGS. 2 and 3. One aspiration needle and one dispenser needle are each preferably arranged in pairs on the washing head 8, so that liquid 10 can be aspirated out of a well 18 and fresh liquid 10 can be dispensed simultaneously via a separate washing needle 5 into the same well 18. Such washing heads 8 are particularly suitable for the indexed washing of 96-well and 384-well microplates. In addition, the use of needle pairs each comprising one aspiration needle and one dispenser needle is preferable, since in this way the conduction of the waste liquids and the fresh washing liquids occurs in separate line systems and the contamination hazard can be decreased accordingly.

Washing heads 8, which only have one washing needle 5 in the simplest embodiment, are not shown in the figures, but are also known and are suitable for performing the method according to the invention. Only one well 18 can be processed at a time using such a washing head 8. In the case of a plurality of wells 18, one well 18 after the other is serviced therewith. Such a simple washing head 8 is suitable, for example, for servicing microplates having only one large well.

Washing heads 8, which each comprise 16 or even 96 or 384 aspiration needles and dispenser needles, are also not shown in the figures but are known from the prior art and are suitable for performing the method according to the invention. Correspondingly, for example, a washing head having 96 aspiration needles and 96 dispenser needles comprises a total of 192 washing needles, so that suctioning can be performed simultaneously in all wells 18 of a standard 96-well microplate 17 and dispensing can be performed without changing the washing head 8. If the diameter of each of these needles is furthermore adapted to the well size of a 384-well microplate, this 96-place washing head can correspondingly also be used for the indexed washing of a 384-well microplate. Such 96-place or 384-place washing heads are particularly preferred for performing the method according to the invention. Washing heads 8 having two separate washing needle systems, i.e., separate washing needles 5 for aspiration and for dispensing, accordingly have two separate channel systems for supplying the respective washing needle system (not shown). The construction of such channel systems is part of the knowledge of a person skilled in the art and will therefore not be further discussed here.

A microplate washing device 2 can typically be equipped with various washing heads 8. Surprisingly, it is possible to show that even if various washing heads 8 on a microplate washing device 2 and various waste containers 1 are used, the same calibration data can be used for registering the filling potential of the waste container 1. This "universality" can be reasoned by the following assumptions:

The method according to the invention is based on a time measurement of a partial vacuum dissipation. This was made possible by opening the valve 7 between the waste container 1 and the washing head 8 and air flowing through the washing needles 5 into the lines 6 and the waste container 1. The open valve 7 is typically the location of the system having the smallest flow cross-section, which therefore limits the inflow quantity. This is the case in particular upon the use of a 96-place standard washing head (having 96 aspiration needles and 96 dispenser needles) or a 96-place indexing washing head (the needles of which are adapted to the size conditions of a 384-well microplate). Each washing needle 5 of these washing heads, when considered alone, does have a smaller flow cross-section than the open valve 7. However, due to the large number of the washing needles, the sum of the needle cross-sections is sufficiently large so that in total a significantly greater flow cross-section is available for air to flow into the system. Thus, a significantly larger quantity of air per unit of time can flow in through the washing needles 5 than can flow through the open valve 7. The channels in the washing head itself are not flow-limiting. This universality would still exist accordingly, if alternatively a valve 7 having a greater flow cross-section and a washing head 8 having a smaller number of washing needles 5 were used, but an artificial constriction was intentionally installed in the line 6 between the washing head 8 and the waste container 1.

As shown in FIG. 1, the simplest embodiment of a microplate washing device 2 suitable for performing the method according to the invention comprises at least one waste container 1, in which suctioned-off liquids 10 are collected. Its shape and size are not decisive for performing the method according to the invention. However, it is important that the waste container 1 is formed to be closable substantially airtight. In addition, the waste container 1 is preferably formed to be suitable for vacuum, i.e., it does not deform when being subjected to a partial vacuum or vacuum. In this way, it can be ensured that a sufficiently low partial vacuum can be applied in the waste container 1 by the suction pump function in order to perform the method according to the invention. The various types of airtight closing are well known to a person skilled in the art. For example, self-sealing threads on the cover 12 and container lower part are mentioned here (see FIG. 1). For example, a screw-on cover can be formed to be elastic, so that a clamping action is additionally used for the sealing. The sealing effect can also be amplified by sealing elements 13 such as rubber seals (not shown). The seal can also be achieved solely by rubber seals, for example, without threads being used (see FIGS. 2 and 3). Such sealing systems are also well known from the prior art.

The shape and size of the waste container 1 comprised in the microplate washing device 2 are not relevant for performing the method according to the invention. Solely as an example, the Nalgene® 10 l bottle, Art. No.: 226-0020 made of polypropylene (Thermo Fisher Scientific, Kamstrupvej 90, 4000 Roskilde, Denmark) is therefore mentioned here. Alternative container materials are glass or also chromium steel, for example. A smaller container of 5 l or 3 l, for example, or alternatively a larger container of 20 l or up to 50 l can also be used as needed.

This independence from the shape and size of the waste container 1 is achieved by determining a threshold time. This threshold time is determined for a defined air residual volume. This air residual volume is a safety volume, with which, no matter how large the employed waste container 1 is selected, it is no longer to be filled. Once this safety volume is determined, it is applied for all usable waste containers 1. Thus, if a safety volume of 3 l is determined, this applies both for waste containers of 5 l total volume and also for those having 20 l or even 50 l total volume. The consideration is in the foreground that no matter how much waste liquid a container can accommodate, an air volume (residual volume) of 3 l is always to remain free for safety. It can thus be ensured in a simple way that the container is not overfilled in any case.

As shown in FIG. 2, the microplate washing device 2 which is suitable for performing the method according to the invention can also comprise two waste containers 1, 33 connected in series one after the other. The second waste container 33, which is at the rear viewed from the washing head 8, is used as a safety container for the case in which the aspirated liquid tends to foam and foam is nonetheless suctioned from the waste container in the direction of the pump by the partial vacuum ("foam trap" 33). This second waste container 33 does provide an additional volume for catching liquids. However, this has no effects on the method according to the invention itself, since, as already mentioned, it is essentially independent from the actual available maximum container volume due to the determination of a "universal residual volume". It is important that this additional volume by the foam trap 33 is registered in a preceding calibration measurement. The pressure curve as a function of time of the partial vacuum dissipation in the waste container 1 and in a previously determined partial vacuum test range does not change in the case of an identical test range but different catch volumes. In fact, the use of an additional, second waste container 34 according to FIG. 2 is even preferred.

It is obvious from FIGS. 1 to 3 that the pump 3 for generating a partial vacuum is connected via a line 6' to the waste container 1, while the waste container 1 is in turn connected via a separate line 6 to the washing needle 5. If the microplate washing device 2 employed comprises a washing head 8 having more than one washing needle 5, the line 6 in the washing head 8 merges into the corresponding channel system mentioned above. This branches corresponding to the number of the washing needles 5, and one branch opens into each washing needle 5. If needle pairs each comprising one aspiration needle and one dispenser needle are used, the washing head 8 comprises two separate channel systems (as an aspiration system and a dispenser system). These are also correspondingly formed to be branched. The arrangement of the necessary lines 6, 6', 6", their dimensions, and the employed materials are well known to a person skilled in the art, and shall therefore not to be discussed further here. Polyvinyl chloride (PVC) is mentioned as an example of a usable material. Such PVC lines have the advantage that they are soft and moldable and can thus be integrated in a space-saving manner in the microplate washing device 2. An internal diameter of 8 mm is also mentioned as an example of usable internal diameters of these lines. This corresponds to a cross-section of 50.26 mm².

The lines used for microplate washing devices 2 have a separate internal volume corresponding to their length and their internal diameter. However, this is very small in comparison to the container volume and is registered during the calibration of the device. Since it is always significantly smaller than the volume of the employed waste container, however, the line volume itself has no relevant influence on the performance of the method according to the invention.

As shown in FIGS. 1 to 3, the microplate washing device 2 comprises a valve 7 on the line 6 between the waste container 1 and the at least one washing needle 5 (or the washing head 8) for performing the method according to the invention. Furthermore, an additional valve 20 is provided between the waste container 1 and the pump 3. This additional valve can be comprised directly by the pump 3, 3', 16, for example. This is the case in FIG. 1, therefore, this additional valve is not explicitly shown in this FIG. 1. For such a pump having an internal valve, for example, the Thomas diaphragm pump of the type 8011 ZVP 35 is mentioned as an example. If the pump 3 used for generating a partial vacuum does not have an internal valve, this additional valve 20 is arranged on the line 6' between the waste container 1 and the pump 3. It is important that after generating a partial vacuum in the waste container 1, the pump-side line 6' to the waste container 1 can be blocked. Suitable valves are simple straight way valves, for example, the 2/2 way valve 0115 from Christian Bürkert GmbH & Co. KG (Christian-Bürkert-Strasse 13-17; 74653 Ingelfingen, Germany).

Preferably, the valve 7 is arranged on the line 6 as close as possible to the washing needle 5 or to the washing head 8. In this way, the directly available flooding volume before the valve 7 can be kept small.

The valve 7 shown in FIGS. 1 to 3 can, according to the method according to the invention, be opened to trigger a partial vacuum dissipation in the waste container. In this variant, the air would flow through the openings of the washing needles 5 into the line 6 and the waste container 1. In FIG. 3, an additional de-aeration valve 34 is shown on a T-part on the line 6 between the valve 7 and the waste container 1. This implementation variant allows air not to flow through the washing needles 5 into the container 1 for the partial vacuum dissipation, but rather through the opened valve 34. In this case, the valve 7 can remain closed. The independence of the method according to the invention from the implementation of the washing head 8 is also provided in this variant. The de-aeration valve 34 is implemented as a two-way valve in this case.

Three different washing heads are presented hereafter, which can be used replaceably with a defined valve (Bürkert solenoid valve type 0115 A6.0) and a defined line:

standard 96-place washing head: 0.9 mm internal diameter per needle;
61 mm² total cross-section;
384-well washing head: 0.5 mm internal diameter per needle;
75.4 mm² total cross-section;
96-well indexing washing head: 0.8 mm internal diameter per needle;
48.2 mm² total cross-section;
valve: 6 mm active diameter
28.3 mm² cross-section
line: 8 mm internal diameter
50.2 mm² cross-section Similarly to the pump 3, the internal pressure sensor 4 which is already provided in the microplate washing device 2 can also be used for performing the method according to the invention. By closing the valve 7, a partial vacuum can be applied in the waste container 1 using the pump 3 for performing the method according to the invention. Thereby, the pressure sensor 4 is arranged operationally linked to the waste container 1 for determining an air pressure. The pressure sensor 4 is preferably positioned on the line 6 between the valve 7 and the waste container 1 (see FIG. 1). A sensor of the SQ253-WET-WET series from Sensor Technics (Sensortechnics GmbH, 82178 Puchheim, Germany) is mentioned as an example of a pressure sensor 4 suitable for performing the method according to the invention.

Basically, it is advantageous if a pressure sensor 4 which is protected against sprayed water or insensitive to sprayed water is used. A sprayed water protection known from the prior art is that the sensor 4 is not attached directly on the line 6, but rather a short additional protective line, which is connected to the line 6, is attached in front of the sensor 4. Such an additional line can be implemented as a T-part, for example.

Alternatively, the pressure sensor 4 can also be arranged in the cover 12 of the waste container 1, as long as it is protected against sprayed water. If two waste containers 1 arranged in series one behind the other are used, one pressure sensor 4 on one of the two covers 12 (see FIG. 2) is sufficient. It is also conceivable that the pressure sensor 4 is not arranged on the cover but rather directly on the waste container 1 (see FIG. 3). However, the positioning of the pressure sensor 4 on the cover 12 or on the waste container 1 has the risk that liquid might reach the sensor 4 and thus functionally impair it. Additional protective structures must possibly be attached in front of the sensor here.

Alternatively, the pressure sensor 4 can also be arranged on the line 6' between the waste container 1 and the suction pump 3. It is important that the pressure sensor 4 is always operationally linked to the waste container such that the air pressure in this waste container can be determined therewith, and that the risk of being restricted in function by liquid sprays is as small as possible. Therefore, the position of the pressure sensor 4 shown in FIG. 1 is the preferred one.

The microplate washing device 2 which is suitable for performing the method according to the invention also comprises, in addition to the pressure sensor 4 which is operationally linked to the waste container 1, a sensor controller 14, which receives and processes the detected data of the pressure sensor 4. The assignment of the sensor controller 14 to device-specific firmware or software is dependent on the electronic organization of the microplate washing device 2 and the employed hardware components and is part of the knowledge of a person skilled in the art. As shown in FIGS. 2 and 3, the microplate washing device 2 suitable for performing the method according to the invention can comprise a filter 11 as a protection of the pump from contaminants, such as liquid which reaches the line to the pump from the waste containers 1. Filters can optionally be used both for suction pumps, combined suction/pressure pumps 3' and pressure pumps 16. A filter is preferably arranged between the pump 3, 3' and the waste container 1. The use of filters for protecting the pumps is also part of the knowledge of a person skilled in the art and is therefore also not explained in greater detail here. For illustration, the filter LYF 0300.008 from Metzger Technik GmbH & Co. KG (Bertha-Benz-Strasse 1, 71655 Vaihingen/Enz, Germany) and the filter SteriVent 002103 from Arbor Technologies (Whatman plc, James Whatman Way, Maidstone, Kent, ME 14 2LE, United Kingdom) are mentioned here as examples; both are suitable filters known from the prior art.

In FIG. 3, a microplate washing device 2 is shown, which has not only the aspiration system but also the dispensing system. As already mentioned, a microplate washing device comprises both the aspiration system and also the dispensing system. An overpressure is generated using a pressure pump 16, using which liquid 10 is transported from a storage container 9 via lines 6" into the washing needles 5 and finally into the wells of a microplate 17 for dispensing. In FIG. 3, a modified microplate washing device 2 is shown, in which a valve 28 of the dispensing system is implemented as a three-way valve. By means of this three-way valve 28, the pressure pump 16 is not only connected to the dispensing system but rather additionally also to the aspiration system. In an alternative embodiment of the method according to the invention, an overpressure can thus be generated in the waste container 1, and it can then be registered via the determination of a test time of an over-pressure dissipation in a predetermined over-pressure test range, whether or not this waste container is still fillable. The selection of the pressure pump is also in the scope of the knowledge of a person skilled in the art here, the pump 72100165M2 from Thomas (Gardner Denver Thomas GmbH, Benzstrasse 28, 82178 Puchheim, Germany) is mentioned as an example here.

FIG. 4 shows a schematic overview of a circuit diagram of a microplate washing device 2, which is suitable for performing the method according to the invention. The microplate washing device 2 comprises a central processing unit 32 (CPU), comprising at least one motor controller, a valve controller, a sensor controller and a pump controller. Using these controllers, for example, the motors 29,30 for the washing head 8 and the plate transport and therefore movements of the washing head 8 and the plate transport are controlled. The vacuum pump and the pressure pump 16 can be controlled via the pump controller. The opening and closing of the valves 28 of the storage container 9 and the valve 7 between washing head 8 and waste container 1 are controlled using the valve controller. If the pumps used comprise internal valves, these are registered by the pump controller. If the pumps used have no internal valves and corresponding valves 20 are arranged on the line 6' before the pump 3, these are also registered by the valve controller. Finally, the data detected by the pressure sensor 4 are received and processed via the sensor controller 14. In addition, an operating panel 27 of the microplate washing device 2 is controlled via the central processing unit 32, and data of the operating panel 27 are processed by the central processing unit 32. The question whether the controller is coded in firmware or software is not relevant for performing the method according to the invention and can vary depending on the requirements for the microplate washing device 2.

The method according to the invention for determining an air volume 15 in a waste container 1 of a microplate washing device 2 is performed using a microplate washing device 2 as was described above. Thereby, the microplate washing device 2 comprises at least one washing needle 5 for aspirating liquids out of a sample vessel, such as, for example, a well of a microplate. In addition, it comprises at least one waste container 1, in which the aspirated liquid 10 is captured and collected. For this waste container, it is to be registered using the method according to the invention whether the waste container 1 can be filled still further by further aspiration, without overflowing. This waste container 1 is closable substantially airtight. This is necessary so that a partial vacuum can be built up in the waste container 1 by the pump 3. The pump 3 of the microplate washing device 2 is connected via a line 6' to the waste container 1, while the waste container 1 is in turn connected via a line 6 to the at least one washing needle 5. For determining an air pressure in the waste container, the microplate washing device 2 furthermore comprises at least one pressure sensor 4 and a sensor controller 14. The pressure sensor 4 is operationally linked to the waste container 1 such that it is suitable for determining the air pressure in this container 1. Finally, the microplate washing device 2 comprises a valve 7 for blocking and opening the line 6 between the at least one washing needle 5 and the waste container 1, while the pump-side line 6' to the waste container can be blocked. As discussed in detail above, the microplate washing device 2 can have additional or alternative features.

The method according to the invention will now be described in greater detail on the basis of FIG. 5. An exemplary pressure curve as a function of time, as is detectable when performing the method according to the invention, is shown here. The pressure specifications in this figure are each specified in relation to the ambient pressure, to which the reference dimension "zero" was assigned accordingly.

For registering, whether or not a waste container 1 is fillable, a partial vacuum test range is first predetermined. For this purpose, two limiting pressures 25,26 are defined, which encompass this partial vacuum test range. These limiting pressures 25,26 characterize the outer two range boundaries and are part of the partial vacuum test range. Both limiting pressures 25, 26 are less than the current ambient pressure: The upper limiting pressure 26 bounds the test range in relation to the ambient pressure. The lower limiting pressure 25 is less than the upper limiting pressure. The limiting pressures 25,26 are preferably stored in the storage medium of the microplate washing device 2, so as to allow an automation of the method according to the invention.

In the measurement shown in FIG. 5, the limiting pressures of the test range were defined as follows:
upper limiting pressure 26: 100 mbar below the ambient pressure;
lower limiting pressure 25: 500 mbar below the ambient pressure.

If the partial vacuum test range has been determined, a partial vacuum is applied in the waste container 1. For this purpose, the valve 7, which is arranged on the line 6 between the at least one washing needle 5 or the washing head 8 and the waste container 1, is closed. The partial vacuum is then built up by turning on the pump 3, which is adapted to generate a partial vacuum. The amount by which the air pressure in the waste container 1 is reduced is dependent on the pump capacity and the selection of the lower limiting pressure 25 of the predetermined partial vacuum test range. For example, if the lower limiting pressure 25 is defined at 600 mbar below the ambient pressure, at least a partial vacuum of 600 mbar below the ambient pressure or less should also be built up using the pump 3. Whether and by how much the built-up partial vacuum is below than the lower limiting pressure 25 is within the knowledge of a person skilled in the art. At least, specific conditions of the device (for example, of microplate washing device 2 and pump 3), as well as the judgment of how much time the performing of the method according to the invention is to occupy, are to be taken into consideration.

The partial vacuum buildup and the time required for this purpose can already be tracked using the pressure sensor 4 and the sensor controller 14. For registering the partial vacuum buildup and dissipation as a function of time, the data measured by the pressure sensor 4 can be analyzed continuously or in pulses, for example, at a frequency of 100 Hz. An exemplary pressure curve of a partial vacuum buildup as a function of time is shown in FIG. 5 from a pressure of approximately 300 mbar below the ambient pressure (t=1 to approximately 3 seconds). It can also be inferred from this FIG. 5 that in this exemplary method, the generated partial vacuum is somewhat below the lower limiting pressure 25 of the partial vacuum test range.

According to the method according to the invention, the judgment of the filling potential of a waste container 1 is essentially based on the analysis of the pressure curve as a function of time of a partial vacuum dissipation in the partial vacuum test range. Alternatively thereto, the partial vacuum buildup in the partial vacuum test range as a function of time can be analyzed: for doing this, e.g. a standard pump preferably is used with constant capacity, so that the time for achieving a certain under-pressure with the pump is also proportional to the free gas volume of the container. In a further alternative to the method according to the invention overpressure is accordingly used instead of partial vacuum. The adaptation of the method according to the invention to these alternative procedures is within the knowledge of a person skilled in the art and will therefore not be described in further detail here.

To generate the partial vacuum dissipation, the valve 20 is first closed. This can be performed by the controller of the pump function itself, for example, if the valve 20 is integrated in the pump 3, for example. Or the closing of the valve 20 is performed via a separate valve controller, e.g., if the valve 20 is arranged on the line 6' separately from the pump 3. The partial vacuum range is locally terminated and bounded by closing the valve 20.

The partial vacuum dissipation in the waste container 1 is finally triggered by the opening 19 of the valve 7, which is arranged on the line 6 between the washing needle 5 or the washing head 8 and the waste container 1. The partial vacuum is dissipated in that air can intentionally flow via the washing needle 5 into the waste container 1. Preferably, a washing head 8 comprising 96 aspiration needles and 96 dispenser needles or comprising 384 aspiration needles and 384 dispenser needles is used for performing the method according to the invention. As already shown, each individual washing needle 5 does have a significantly smaller internal diameter than the line 6 or the open valve 7 and would thus represent—when considered alone—the "bottleneck" for the air volume which can flow in. In contrast, the sum of all aspiration and dispenser needles provided in an employed washing head 8 provides a total flow cross-section, which is significantly greater than the flow cross-section of the line 6 and that of the opened valve 7. Thus, the valve 7 is the element which limits the inflowing air volume in the microplate washing device 2. Correspondingly, however, the line 6 can also be the element which limits the inflowing air volume, if a valve 7 is used which, when opened, has a larger flow cross-section than the employed line 6. In any case, this means that the temporal behavior of the partial vacuum dissipation is not dependent on the washing head employed, and can therefore be performed by any suitable microplate washing device 2 independently of the employed washing head 8—as long as the washing needles 5 of this washing device 2 are not the element which limits the air flow.

If the microplate washing device 2 has an additional de-aeration valve 34 between the valve 7 before the washing head 8 and the waste container 1, as shown in FIG. 3, the partial vacuum dissipation in the waste container 1 can alternatively be triggered by opening this de-aeration valve 34. The valve 7 remains closed. In this case, both valves 7, 34 would correspondingly have been closed for the preceding generation of the partial vacuum in the waste container 1. It is decisive that even if this additional de-aeration valve 34 is used, the independence from the employed washing head 8 is maintained. Here, the "bottleneck" for the air volume which can flow in is similarly either the valve 7 or the de-aeration valve 34.

For analyzing the pressure curve as a function of time during the partial vacuum dissipation, the pressure in the waste container 1 and the test time 21 for the partial vacuum dissipation between the lower limiting pressure 25 and the upper limiting pressure 26 of the partial vacuum test range are measured. Such a measured exemplary pressure curve is shown in FIG. 5: upon the opening 19 of the valve 7, air flows into the waste container 1, and the pressure in this container approaches the ambient pressure. Thereby, the test time 21 corresponds to the time window Δt for the partial vacuum dissipation, measured from the passing of the lower limiting pressure 25 until reaching the upper limiting pressure 26.

For registering, whether or not the waste container 1 is still fillable, the test time 21 measured for this waste container 1 is compared to a threshold time 22 determined before the measurement. This threshold time 22 is preferably determined for a specific microplate washing device 2; it was measured beforehand in a separate calibration measurement for an arbitrarily defined safety residual volume and the partial vacuum test range selected for the test time 21. This safety residual volume is determined such that it can be applied for all usable waste containers 1, independently of their shape and size. A previously measured time for a partial vacuum dissipation of a freely selected waste container 1 having a defined safety residual volume, by which the waste container 1 of the microplate washing device 2 is no longer to be filled, is thus determined more or less universally for the microplate washing device 2 according to the method according to the invention. The condition for this "universality" is that the same partial vacuum test range and the same arrangement and dimension of valve 7 and line 6 are used for the calibration measurement and the test measurements. Further, if a microplate washing device 2 having a so-called foam trap 33, i.e., having a second downstream "safeguard waste container", is used, this additional air volume must accordingly also be registered in the calibration measurement. The test time 21 can thus be correlated directly with the safety residual volume of the threshold time 22, without that the volume of the foam trap 33 has to be included separately in the comparison.

If the comparison of a test time 21 measured for a waste container 1 having an essentially unknown degree of filling with the previously defined threshold time 22 has the result that the test time 21 falls below the threshold time 22, it is decided that the waste container 1 is not fillable. This constellation indicates that only an air volume is still present in the waste container 1 which is less than the previously arbitrarily determined safety residual volume. In contrast, if this comparison has the result that the test time 21 is equal to the threshold time 22 or exceeds it, it is decided that the waste container 1 is fillable. In this case, the air volume present in the waste container 1 is greater than the safety residual volume, and thus an (undefined) liquid quantity can still be aspirated into the waste container 1.

The method according to the invention is therefore based on a partial vacuum test range which is applied both for the calibration measurement(s) and the actual test measurement(s). In order to allow a meaningful, analyzable time measurement for a partial vacuum dissipation in the partial vacuum test range, this test range should encompass at least 100 mbar. The size of the test range is left to a person skilled in the art. By expanding this test range, the measurement accuracy can be improved up to a certain extent. In contrast, however, it is to be considered that a very long time measurement is not necessarily reasonable for a user of the microplate washing device 2. In particular, a balance is to be made between the available (customer) time and measurement precision. The partial vacuum test range preferably encompasses 200 mbar, particularly preferably 400 mbar. However, for an according pump capacity, it can encompass up to 950 mbar.

The partial vacuum test range is defined by the selection of the lower limiting pressure 25 and the upper limiting pressure 26. The upper limiting pressure 26 is preferably separated by at least 50 mbar from the ambient pressure. It can thus be ensured that no pressure variations are detected in the test range, but rather a continuous pressure buildup (i.e., a continuous partial vacuum dissipation) is measurable. Such pressure variations are visible in FIG. 5; for example, they may be measuring artifacts, triggered by the limits of the measuring precision of the pressure sensor. The upper limiting pressure 26 is preferably selected from a pressure range of 50 mbar to 300 mbar below the ambient pressure, the upper limiting pressure 26 is particularly preferably 100 mbar below the ambient pressure. FIG. 5 shows a partial vacuum test range having this particularly preferred upper limiting pressure 26 of 100 mbar below the ambient pressure.

The lower limiting pressure 25 is determined substantially based on the pump capacity and the preferred size of the test range. The lower limiting pressure 25 is preferably selected from a pressure range of 800 mbar to 150 mbar below the ambient pressure. The lower limiting pressure 25 is particularly preferably 500 mbar below the ambient pressure. FIG. 5 shows a partial vacuum test range having this particularly preferred lower limiting pressure 25 of 500 mbar below the ambient pressure.

The two limiting pressures 25, 26 which define the partial vacuum test range are preferably stored in a storage medium of the microplate washing device 2. For example, an EPROM (erasable programmable read-only memory) is mentioned here. This storage medium therefore belongs to the device, for example, to the central processing unit 32. The selection and arrangement of the storage medium is within the knowledge of a person skilled in the art. Preferably, the storage is performed by the manufacturer, but can also be performed by the user in case of a corresponding need. Furthermore, the storage can be performed in a device firmware or software. The storage in a device firmware has the advantage that these limiting pressures 25, 26 are only determined once, and the user can cause the method according to the invention to be executed automatically by the microplate washing device 2 without additional expenditure. If the user or also the manufacturer is to be given the possibility of being able to change the limiting pressures 25, 26, the storage in software is preferred. The selection is also in the scope of the knowledge of a person skilled in the art according to the requirements for the microplate washing device 2 and the method according to the invention.

FIG. 6 shows schematically the relationship between various residual volumes in a waste container 1 and the corresponding measurable times in a defined partial vacuum test range. The method according to the invention is based on the fact that for a specific residual volume, the same time of the partial vacuum dissipation is substantially always measurable in the same partial vacuum test range, independently of the actual container size. Correspondingly, a "universal" threshold time 22 can be established for a partial vacuum test range, which applies for substantially all waste containers 1 usable in the microplate washing device.

The threshold time 22 is preferably the time of a partial vacuum dissipation in the partial vacuum test range for a residual volume of a waste container 1, which is selected from a volume range of 1.5 l to 4.5 l. Such a residual volume is applicable for waste containers 1 having a maximum filling volume of, for example, 5 l up to 50 l, for example. The threshold time 22 is particularly preferably established for a residual volume of a waste container 1 of 3 l. Such a threshold time $t_{(22)}$ is shown in FIG. 6.

The threshold time 22 is preferably stored in the storage medium of the microplate washing device 2. If the comparison of a measured test time 21 to the established threshold time 22 yields the result that the waste container 1 is no longer fillable, a signal for changing or emptying the waste container 1 is preferably triggered. The triggering is typically performed via a controller (for example, via a processor of the central processing unit 32). This signal can be an according notification in the display 27 of the microplate washing device 2. Alternatively, lighting up a colored light on the device 2 is also possible. Such signals are known from the prior art and will therefore not be discussed further here.

In a preferred variant of the method according to the invention, a first tolerance time 23 is also established before the measurement of the test time 21. Analogously to the threshold time 22, this first tolerance time 23 is determined in a preceding calibration measurement. It is the time of a partial vacuum dissipation in the partial vacuum test range for a residual volume which is larger than the residual volume for the threshold time 22. The residual volume for the first tolerance time 23 is preferably greater than the residual volume for the threshold time 22 by a volume selected from a volume range of 1 l to 2 l.

Such a first tolerance time $t_{(23)}$ for an exemplary residual volume of 4 l is shown in FIG. 6. This first tolerance time 23 represents an additional safety step for the aspiration process using the microplate washing device 2: If the test time 21 measured for a waste container 1 having unknown filling volume falls below the first tolerance time 23, but is greater than the threshold time 22, it is decided that the waste container 1 is fillable. The first tolerance time 23 is preferably stored in the storage medium of the microplate washing device 2. If the comparison of the test time 21 with the threshold time 22 and the first tolerance time 23 yields the result that the waste container is fillable, a filling quantity of 1 l or 2 l of liquid can be made available, for example. This making available can occur internally in the device, for example, it can alternatively or additionally also be communicated to the user via the display 27 of the microplate washing device 2. The making available is preferably also performed by the controller. The quantity made available is a maximum liquid quantity, which is arbitrarily established by the manufacturer or by the user, and which is to be aspirated by the microplate washing device 2 and transferred into the waste container 1. The determination is within the knowledge of a person skilled in the art; thereby, for example, the need and the microplate washing device 2 or the available washing programs are considered.

In a further preferred variant of the method according to the invention, a second tolerance time 24 is further determined before the measurement of the test time 21. Similarly to the threshold time 22, this second tolerance time 24 is determined in a preceding calibration measurement. It is the time of a partial vacuum dissipation in the partial vacuum test range for a residual volume which is greater than the residual volume for the threshold time 22. The residual volume for the second tolerance time 24 is preferably greater than the residual volume for the threshold time 22 by a volume selected from a volume range of 3 l to 10 l.

In FIG. 6, such a second tolerance time $t_{(24)}$ for an exemplary residual volume of 10 l is shown. This second tolerance time also represents an additional safety step for the aspiration process using the microplate washing device 2. It can therefore be determined in combination only with the threshold time 22 or in combination with the threshold time 22 and the first tolerance time 23 for the method according to the invention:

If the second tolerance time 24 is only determined in combination with the threshold time 22, and if the test time 21 is greater than or equal to the second tolerance time 24, it is decided that the waste container 1 is fillable. Preferably, the second tolerance time 24 is stored in the storage medium of the microplate washing device 2. If the comparison of the test time 21 to the second tolerance time 24 yields the result that the waste container is fillable, for example, a filling quantity of 4 l is made available. This making available can again be performed internally in the device, and/or communicated to the user via the display 27 of the microplate washing device 2. The making available is preferably also performed by the controller. This quantity made available is also a maximum liquid quantity arbitrarily determined by the manufacturer or the user, which is to be aspirated by the microplate washing device 2 and transferred into the waste container 1.

If the second tolerance time 24 is determined in combination with the threshold time 22 and the first tolerance time 23 (see FIG. 6), the filling potential of the waste container 1 is first also decided via the comparison of the test time 21 to the second tolerance time 24. Also here, the threshold time 22, the first tolerance time 23 and the second tolerance time 24 are preferably stored in the storage medium of the microplate washing device 2 here. Furthermore, a more differentiated decision can then be made for the following aspiration processes: If the test time 21 falls below the second tolerance time 24, but is greater than or equal to the first tolerance time 23, for example, a filling quantity of 2 l can be made available. This making available can also be performed internally in the device (e.g., by the central processing unit 32), and/or communicated to the user via the display 27 of the microplate washing device 2; this quantity made available is also a maximum liquid quantity arbitrarily determined by the manufacturer or by the user, which is to be aspirated by the microplate washing device 2 and transferred into the waste container 1.

In FIG. 6, a function 31 for the time of a partial vacuum dissipation of a predetermined partial vacuum test range and various residual volumes in a waste container 1 is shown as an example. If the corresponding times are measured in one calibration measurement each for various defined residual volumes, as in this case for 3 l, 4 l, and 10 l of residual volume, such a calibration function 31 can be established. At least two measured times of a partial vacuum dissipation in the predetermined partial vacuum test range are mathematically necessary for this purpose. Such a calibration function 31 can be based on a threshold time 22 and a second tolerance time 24, for example, however, other measured times can also be used alternatively. On the basis of such a calibration function 31, it can then be determined for a test measurement for a waste container 1 having unknown residual volume how large the actual residual volume is, by which this waste container 1 is still fillable. Similarly or alternatively, the current liquid quantity present in this waste container 1 can also be determined. For this purpose, however, the maximum container volume of this waste container 1 should be known. Preferably, one measured time used for the calibration function 31 is the threshold time 22.

Preferably, the threshold time 22, the first tolerance time 23 and the second tolerance time 24 are determined once by the manufacturer for a microplate washing device 2 and stored. It is also preferred for the method according to the invention, in particular that the measurement of the test time is performed automatically during the use of this microplate washing device 2. For example, it can be indicated to the user via the display 27 when the method is performed; however, it is also conceivable that the performing of the method according to the invention is performed "autonomously in the device" and without information to the user by the microplate washing device 2. The performing of the test time measurements and the making available of filling quantities are particularly preferably performed "autonomously in the device", while if it is established that the waste container 1 is no longer fillable, this is communicated to the user (for example, by a signal or a display).

The method according to the invention was described hereinbefore using a suction pump function and a partial vacuum. In fact, it is also possible to perform the method according to the invention employing overpressure. One condition for this is that the microplate washing device 2 comprises a pressure pump 16 or at least a pressure pump function. As already discussed, the pressure pump function can be provided by a combined suction/pressure pump 3'. Furthermore, one condition is that the pressure pump 16 or the combined suction/pressure pump 3' is connected via lines 6" to the at least one waste container 1 and the washing needle(s) 5. In each of FIGS. 2 and 3, an exemplary schematic construction of a microplate washing device 2 is shown, using which the method according to the invention can be performed employing overpressure by means of a combined suction/pressure pump 3' (FIG. 2) or a separate pressure pump 16 (FIG. 3). Alternatively, the pressure curve as a function of time of a partial vacuum or overpressure buildup can also be used as a measure of the filling potential of a waste container 1.

The method according to the invention can be used not only for determining an air volume 15 in a waste container 1 of a microplate washing device 2, or the residual volume or the current fill level in this container 1. It is also possible to perform a tightness test of the line system of the microplate washing device 2 by employing this method. The test can be based on a comparison a) of a measured test time $\Delta t$ for a defined waste container 1 having a known air volume 15 using b) known test times of a comparison table for the same waste container 1 having equal air volume 15. If the system is tight, the currently measured test time should substantially correspond to the known test time stored in the device firmware. In contrast, if there is a leak in the system, either the partial vacuum or overpressure applied to perform the method cannot be achieved at all. If the partial vacuum or overpressure is achieved, the test time for passing through the correspondingly defined test range is shortened, since air can additionally flow through the leak into the system and thus accelerate the pressure equalization. If a filter is arranged between the pump and the waste container and clogs, or if the pump is defective, the time until reaching the partial vacuum or overpressure is lengthened.

The reference signs in the figures each indicate identical elements, even if they are not described in detail in each case. The list of reference signs is part of the disclosure.

| List of reference signs: | |
| --- | --- |
| 1 | waste container |
| 2 | microplate washing device, washer |
| 3 | pump having suction function |
| 3' | combined suction/pressure pump |

-continued

List of reference signs:

| | |
|---|---|
| 4 | pressure sensor |
| 5 | washing needle |
| 6, 6', 6" | lines |
| 7 | valve |
| 8 | washing head |
| 9 | storage container |
| 10 | liquid |
| 11 | filter |
| 12 | cover |
| 13 | seal |
| 14 | sensor controller |
| 15 | air volume |
| 16 | pressure pump |
| 17 | microplate |
| 18 | wells of the microplate |
| 19 | opening the valve |
| 20 | valve |
| 21 | test time |
| 22 | threshold time |
| 23 | first tolerance time |
| 24 | second tolerance time |
| 25 | lower limiting pressure of the partial vacuum test range |
| 26 | upper limiting pressure of the partial vacuum test range |
| 27 | operating panel/display of 2 |
| 28 | valve of 9 |
| 29 | motor for plate transport |
| 30 | motor for washing head |
| 31 | calibration straight line |
| 32 | central processing unit |
| 33 | foam trap |
| 34 | valve |

What is claimed is:

1. A method for registering the filling potential of a waste container (1) of a microplate washing device (2), the microplate washing device (2) at least comprising:

a washing needle (5) for aspirating liquids (10);

said waste container (1), being closable substantially airtight, for catching aspirated liquids (10);

a pump (3) for generating a partial vacuum in the waste container (1), wherein the pump (3) and the washing needle (5) are each connected via at least one line (6,6') to the waste container (1); and a pressure sensor (4), which is operationally linked to the waste container (1) for determining an air pressure therein, and a sensor controller (14);

wherein the microplate washing device (2) further comprises a valve (7) for blocking the line (6) between the washing needle (5) and the waste container (1);

wherein the method comprises the following steps:

a) defining a threshold time (22) for an arbitrarily defined safety residual volume in a waste container (1) measured beforehand in a separate calibration measurement, which threshold time (22) is the time for a partial vacuum dissipation within a predetermined partial vacuum test range for the safety residual volume of a waste container (1)

(b) closing the valve (7) between the washing needle (5) and the waste container (1) and generating a partial vacuum in the waste container (1) at least to a lower limiting pressure (25) of the predetermined partial vacuum test range;

c) blocking the pump-side line (6') to the waste container (1);

d) opening the valve (7) between the washing needle (5) and the waste container (1) and triggering a partial vacuum dissipation in the waste container (1);

e) measuring the pressure in the waste container (1) and measuring a test time (21) for the partial vacuum dissipation between the lower limiting pressure (25) to an upper limiting pressure (26) of the partial vacuum test range, wherein the upper limiting pressure (26) is less than the ambient pressure;

f) comparing the measured test time (21) to the threshold time (22) established before the measurement, and g) deciding that:
   (g1) the waste container (1) is not fillable, if the test time (21) falls below the threshold time (22), or
   (g2) the waste container (1) is fillable, if the test time (21) is equal to the threshold time (22) or
   (g3) the waste container (1) is fillable, if the test time (21) exceeds the threshold time (22);

and wherein, prior to the measurement of step e):

i) a first tolerance time (23) is established, the first tolerance time (23) being the time of a partial vacuum dissipation in the partial vacuum test range for a residual volume of a waste container (1) which is larger by a first volume than the residual volume for the safety residual volume defined in step a) for the threshold time (22); and ii) a second tolerance time (24) is determined, the second tolerance time (24) being the time of a partial vacuum dissipation in the partial vacuum test range for a residual volume of a waste container (1) which is greater by a second volume than the sum of the safety residual volume defined in step a) for the threshold time (22) with the first residual volume for the first tolerance time (23).

2. The method according to claim 1, wherein the safety residual volume of a waste container (1) for the threshold time (22) is selected from a volume range of 1.5 l to 4.5 l.

3. The method according to claim 2, wherein the safety residual volume of a waste container (1) for the threshold time (22) is 3 l.

4. The method according to claim 1, wherein the microplate washing device (2) further comprises a storage medium, in which the limiting pressures (25, 26), the threshold time (22), the first tolerance time (23) and the second tolerance time (24) are stored.

5. The method according to claim 1, wherein the first volume is selected from a volume range of 1 l to 2 l.

6. The method according to claim 1, wherein the second volume is selected from a volume range of 3 l to 10 l.

7. The method according to claim 6, wherein the second tolerance time (24) is determined for a residual volume of a waste container (1), which is 7 l greater than the safety residual volume for the threshold time (22).

8. The method according to claim 1, wherein based on at least two measured times of a partial vacuum dissipation in the predetermined partial vacuum test range, a calibration function (31) is established, on the basis of which the current residual volume of the waste container (1), by which it is still fillable, or the current liquid quantity in this waste container (1) is determined, at least one of the measured times being the threshold time (22).

9. The method according to claim 1, wherein the lower limiting pressure (25) of the partial vacuum test range is selected from a pressure range of 800 mbar to 150 mbar below the ambient pressure, and the upper limiting pressure (26) is selected from a pressure range of 50 mbar to 300 mbar below the ambient pressure, but in no instance is the lower limiting pressure the same or higher than the upper limiting pressure.

10. The method according to claim 9, wherein the lower limiting pressure (25) is 500 mbar below the ambient pressure and the upper limiting pressure (26) is 100 mbar below the ambient pressure.

11. The method according to claim 1, wherein in the case of:
- g1) a signal for changing or emptying the waste container (1) is triggered; or
- g2) a filling quantity is made available, if the test time (21) is equal to the threshold time (22); or
- g3) a filling quantity is made available, if the test time (21) exceeds the threshold time (22).

12. The method according to claim 2, wherein in the case of g3):
- and if the test time (21) also falls below the first tolerance time (23), a filling quantity of 1 l of liquid is made available; or
- and if the test time (21) exceeds or is equal to the first tolerance time (23) and falls below the second tolerance time (24), a filling quantity of 2 l of liquid is made available; or
- and if the test time (21) exceeds or is equal to the second tolerance time (24), a filling quantity of 4 l of liquid is made available.

13. The method according to claim 1, wherein the measurement of the test time is performed automatically.

14. The method according to claim 11, wherein the respective filling quantity is automatically made available.

15. The method according to claim 1, wherein the method is performed automatically and autonomously in the device.

* * * * *